United States Patent
Welch

(10) Patent No.: US 7,836,527 B2
(45) Date of Patent: Nov. 23, 2010

(54) COUNTER TOP LOCATED APPLIANCE AND PRESSURIZED FLUID SUPPLY APPARATUS THEREFOR

(76) Inventor: Ronald E. Welch, 1780 Old Glen St., San Marcos, CA (US) 92078

(*) Notice: Subject to any disclaimer, the term of this patent is extended or adjusted under 35 U.S.C. 154(b) by 1065 days.

(21) Appl. No.: 11/529,094

(22) Filed: Sep. 28, 2006

(65) Prior Publication Data

US 2008/0078021 A1 Apr. 3, 2008

(51) Int. Cl.
*E03C 1/04* (2006.01)
(52) U.S. Cl. .............................. 4/675; 4/691
(58) Field of Classification Search ............. 4/675–680, 4/684, 685, 688–692; 601/155, 162, 165; 239/289, 583, 541, 525
See application file for complete search history.

(56) References Cited

U.S. PATENT DOCUMENTS

| 988,504 | A | * | 4/1911 | Pride .............................. 4/677 |
| 1,607,507 | A | * | 11/1926 | Blauvelt ........................ 4/677 |
| 2,096,602 | A | * | 10/1937 | Weingarten .................... 4/676 |
| 2,855,930 | A | | 10/1958 | Blankfield |
| 3,468,306 | A | | 9/1969 | Heitzman |
| 3,593,707 | A | | 7/1971 | Pifer |
| 5,772,616 | A | | 6/1998 | Competiello et al. |
| 6,783,364 | B1 | | 8/2004 | Juan |
| 6,835,181 | B2 | | 12/2004 | Hippensteel |
| 2005/0096573 | A1 | | 5/2005 | Liu |
| 2006/0042006 | A1 | * | 3/2006 | Thomas ......................... 4/678 |
| 2006/0079818 | A1 | | 4/2006 | Yande |
| 2006/0085906 | A1 | * | 4/2006 | Tan et al. ....................... 4/678 |

FOREIGN PATENT DOCUMENTS

EP 0 322367 A1 6/1989

* cited by examiner

*Primary Examiner*—Khoa D Huynh
(74) *Attorney, Agent, or Firm*—Donn K. Harms

(57) ABSTRACT

A conduit for communication of a pressurized water or fluid supply to a counter top appliance above a sink having a faucet providing water to the sink. The device features an elongated rod having an axial passageway for communication of a fluid when engaged through the drain rod aperture of a faucet. The rod has an exterior circumference sized to translate in the aperture and operate the drain closure apparatus on the sink. A pulsating dental cleaning appliance or water dispenser or knob are engageable to the top end of the rod which is adapted on a bottom end under the sink to engage with a pressurized fluid supply. The device may be provided for retrofit through existing faucets by replacing the drain rod, or with new faucets to provide a route for pressurized fluid above a counter top without having to drill holes in the counter top.

8 Claims, 1 Drawing Sheet

COUNTER TOP LOCATED APPLIANCE AND PRESSURIZED FLUID SUPPLY APPARATUS THEREFOR

FIELD OF THE INVENTION

Figure 1:
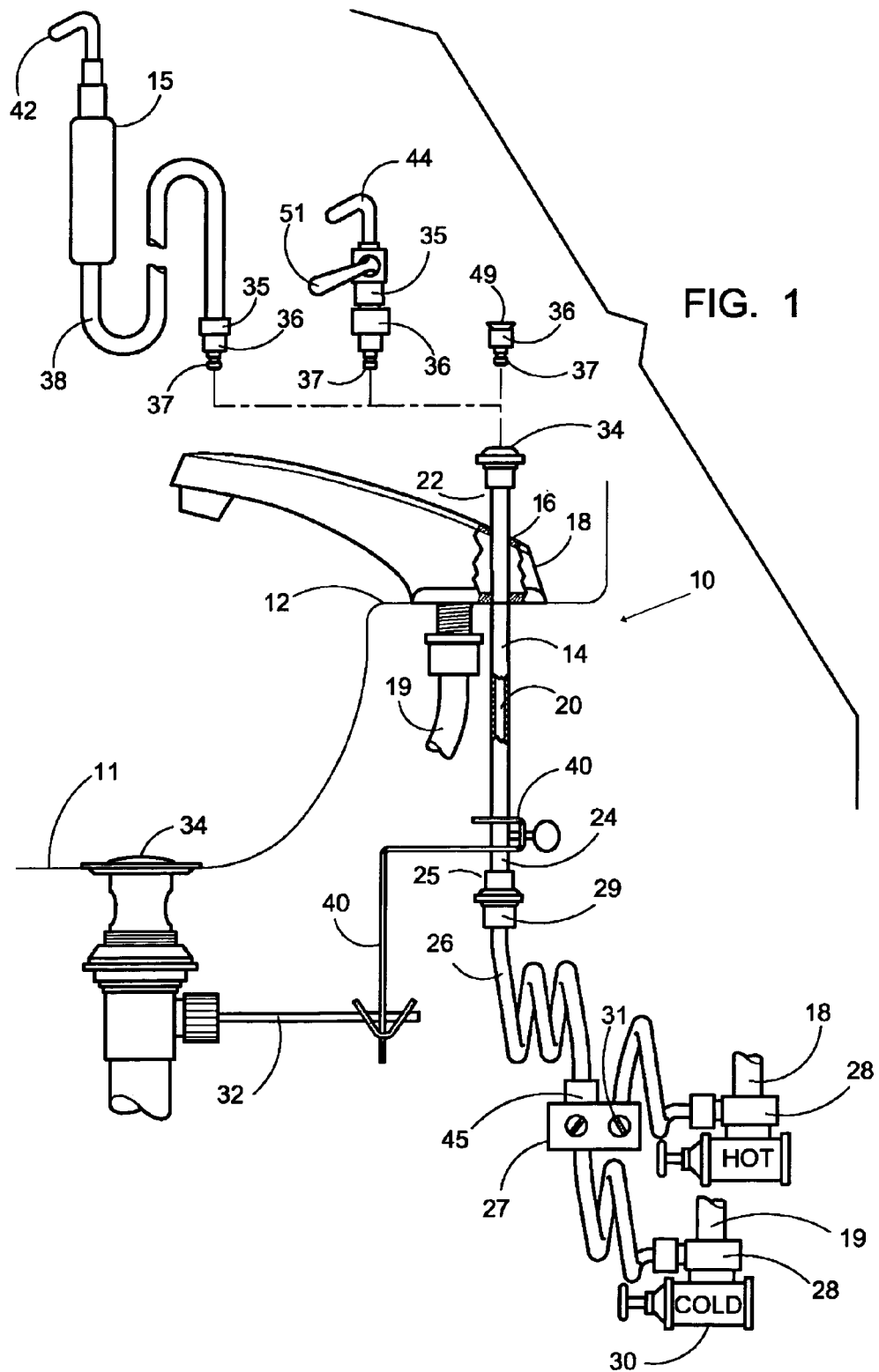

This invention relates generally to oral hygiene and health. More particularly, it relates to appliances such as water jet powered devices and a supply conduit employing an adaptor allowing for communication of a pressurized fluid supply directly from under the counter mounted sink without the need to drill or form apertures though the counter or sink. Additionally, the device can be provided as a retrofit to existing faucets employing elongated drain rods, or it can be employed with new faucets to provide pressurized fluid or a water supply above the sink without the need for holes in the counter or sink.

BACKGROUND OF THE INVENTION

A number of oral hygiene devices are conventionally available which function for oral cleansing and gum massage which employ a variable pressure stream of fluid. Such devices are designed to cleanse the mouth using water pressure to irrigate food and other debris from between the teeth and gums. The varying stream also has the additional benefit of massaging the gums of the user and increasing bloodflow thereto.

One of the best known devices currently on the market is the Waterpik oral irrigator (see U.S. Pat. Nos. 4,302,186; 4,229,634; 4,337,040; and 4,989,590). Most such Waterpik systems and those of many other manufacturers employ an electrically powered pump which imparts varying fluid pressure to a fluid stream communicated to a user-held handle through a flexible hose. In use, the pump is activated and water or other liquid is extracted from a reservoir having a finite supply therein. It is then pressurized by the pump and communicated through a hose to a handle where it is dispensed in a fluid stream at the distal end of the handle. This fluid stream is directed by the user to various positions in the mouth in order to flush particulate matter from the teeth and gums and to concurrently massage the gums.

The reservoir included with most such reservoir-supplied systems is dimensioned to hold sufficient water or other cleaning fluid to last through several cleanings using the system. Although the Waterpik is a popular and effective oral cleansing device, the limited reservoir supply is a vexing problem requiring constant refilling. Another potential problem with this system is that the leftover liquid in the reservoir may become stagnant between cleanings, which can be unsanitary and impart an odor to the room the device occupies.

In order to maintain the fluid in the reservoir in a sanitary manner in reservoir-supplied water ejection systems, many users opt to change the liquid frequently or fill the reservoir with fresh water or cleaning fluid immediately prior to each use. This can be very inconvenient and time consuming, and can increase operating costs if a fluid other than water is employed.

Further, the physical dimensions of such pressurized water or fluid dispensing devices, which is dictated by the inclusion of a fluid reservoir, tend to have an inherently large footprint relative to the small confines of most bathroom counter tops. With the other hygiene and beauty items which also compete for counter top space such as electric toothbrushes, hair dryers, curlers and makeup kits, little space is left for devices which employ a large reservoir that must be placed near or adjacent to an electrical outlet.

Finally, while there are other devices that provide for under-counter mounting, they also require that the counter itself be modified to provide a passage for the water supply conduit. In expensive counter tops such as granite or marble, this is a problem that can cost the homeowner a large expense for professional installation. Even in less expensive construction, the cutting of the proper sized aperture in the counter top is beyond the abilities of most homeowners, thereby requiring them to seek professional help.

U.S. Pat. No. 3,593,707 (Pifer) teaches an oral hygiene device that dispatches with the need for a reservoir or counter top modification. Pifer teaches a toothbrush with a jet nozzle at the end of a detachable handle. The handle is fed by flexible fluid duct from the hot and cold water spigot. A dentifrice is employed with Pifer from another source or from a reservoir connected by a separate duct to the jet brush attachment. Pifer, however, attaches to the end of the faucet which is unsightly and places the water conduit over the sink where it is in the way and subject to damage. The Pifer device also adds a reservoir to the counter top in another mode which as noted is a problem in itself.

Pre-grant application No. 2006/0079818 (Yande) provides a water pulsing for a dental hygiene that connects to one or both water supply lines of the faucet. However, Yande provides no solution other than cutting a hole in the counter top to communicate the handle above the sink. Further, once in such a position, Yande is not easily disconnected nor adapted to other uses.

As such, there exists a need for an apparatus that will allow connection of a water jet oral hygiene device above the counter top in a bathroom. Such a device should allow for the elimination of a reservoir if desired by providing a pressurized water supply to the hose feeding the water hygiene device. Such a device should provide for refilling a reservoir if desired by the user. Still further, such a device should provide the user with a connection means that is disengageable, and alternately engageable with other water supplied devices such as a drinking water dispenser. Further, such a device should be easily adaptable to existing faucet installations which employ drain rod controls, or, provideable with new faucets as a complete unit. Finally, such a device should provide a sealed conduit pathway for water or liquid from below the counter top to the surface above the counter top, without the need to retrofit or cut holes in the counter top, thereby rendering the device easy to install.

With respect to the above description, before explaining at least one preferred embodiment of the invention in detail, it is to be understood that the invention is not limited in its application to the details of construction and to the arrangement of the components or steps set forth in the following description or illustrated in the drawings, nor just to the preparation of food. The various apparatus and methods of the invention are capable of other embodiments and of being practiced and carried out in various ways which will be obvious to those skilled in the art once they review this disclosure. Also, it is to be understood that the phraseology and terminology employed herein are for the purpose of description and should not be regarded as limiting.

As such, those skilled in the art will appreciate that the conception, upon which this disclosure is based, may readily be utilized as a basis for designing of other devices, methods and systems for carrying out the several purposes of the present disclosed device. It is important, therefore, that the objects and claims be regarded as including such equivalent construction and methodology insofar as they do not depart from the spirit and scope of the present invention.

Further objectives of this invention will be brought out in the following part of the specification, wherein detailed description is for the purpose of fully disclosing the invention without placing limitations thereon.

SUMMARY OF THE INVENTION

The device herein described and disclosed provides a sealed conduit for pressurized or other fluid from below a sink or counter top to the surface above, without the need to cut a hole or pathway through the counter top or sink itself. Also provided in the preferred mode is a water jet oral hygiene device feature engageable with the fluid conduit which also may be engaged to a water dispenser and a decorative grip knob. The pressurized fluid for the oral hygiene device as well as any other engaged component is provided using a novel elongated member having a fluid passage axially located therein, the device engages through the drain rod aperture which communicates through conventional bathroom and lavatory faucets. The elongated member might also be provided adapted for sealed engagement with existing oral hygiene devices so the user might retrofit such devices to eliminate the reservoir, or relocate it below the counter top. Further, new faucets may be manufactured using the novel fluid passage running axially in the drain rod which may be adapted on the upper end for engagement to an oral hygiene device or other components that sealably engage thereto.

In all embodiments of the device, an elongated member is provided having a first end of the elongated member which is positioned above the counter top once installed. The first end is adapted for sealed engagement with a hose or flexible conduit which feeds a fluid supply to an oral hygiene or other appliance requiring fluid to operate such as a Waterpik or a drinking water dispenser for purified water. The engagement at the first end may be permanent; however, in the particularly preferred mode of the device, a removable self-sealing engagement is provided to allow engagement to and removal from one or a plurality of water using devices. This removable engagement allows not only for removal of all engaged components when not in use for a more aesthetic appearance of the sink but also allows for engagement of multiple components instead of just a single water using device.

In the preferred mode allowing for removable engagement, the first end or upper end has an engagement aperture therein, communicating with an axial fluid passage which communicates through the entire elongated member. In this preferred mode, the engagement aperture is adapted for a sealed, removable engagement with a nipple or plug. Similarly configured plugs engageable to the aperture may be located on the distal end of the hose communicating with the oral hygiene device requiring water or fluid or on other devices requiring water or pressurized fluid that can be communicated from under the sink.

The plug employed is engageable into the engagement aperture in a removable sealed engagement with the fluid passage running axially through the elongated member. Spring loading of the first end aperture with appropriate releasable connections to hold the nipple in a sealed engagement through an "O" ring works well and such connections are conventionally available. This first end is also dimensioned with a lip or wider portion to allow for easy gripping and pulling by the hand of a user to operate a drain plug of a conventional sink drain.

The second end of the elongated member, opposite the first end, is adapted for engagement with a flexible tube or conduit, which communicates with a pressurized fluid or water supply. This engagement may be threaded or may be similar to the removable engagement at the first end. Since this second end is generally out of eyesight, it is important that a good seal be obtained between the flexible tube and the second end to avoid leaking of pressurized fluid which might cause damage which would be unnoticed over time.

In the kit embodiment of the device, an appropriate flexible conduit adapted to engage the second end would be provided. The conduit must be flexible since the elongated member is employed to operate the drain of the sink through the aperture in the faucet, and thus translates. A means to engage the water supply conduit and communicate pressurized water would also be provided in the form of a fitting adapted for sealed engagement between the flexible conduit and the water supply of the house or building under the counter. Alternatively, the other end of the flexible conduit can be engageable with a reservoir and pump that would be locatable below the counter top. This would allow for a retrofit of an existing hygiene appliance, to relocate the reservoir without the need to drill or otherwise form holes in the counter top. Or, the device would be provided with a reservoir adapted to provide pressurized fluid to the flexible conduit communicating with the axial passage in the elongated member.

A portion of the elongated member between the first end and second end is adapted about its circumference for operative engagement with a drain plug activation rod of a conventional sink drain. Most such engagements of conventional drain rods and drain activation rods employ an angled member which is compressibly engaged to the drain rod with a thumb screw and use a spring clip to connect to the drain plug activation rod. The elongated member with the proper exterior circumference and length would provide the same utility. Provision for passage of the elongated member through existing angled members can be provided by a threaded engagement of the second end with fitting engaging the flexible tube or conduit. The fitting being removable would allow for easy sliding engagement of the second end through the angled bracket during installation. Alternatively, an angled bracket can be provided already attached adjacent to the second end, which would be dimensioned to replace an existing angled bracket. In this case, the fitting on the second end could be permanently engaged or not easily removable for a more dependable seal. Or, other means to operatively engage to the drain activation member can be provided as would occur to those skilled in the art.

The device, when provided as an entire oral hygiene unit would also provide the handle mounted water jet hygiene component which would receive pressurized fluid from the first end of the elongated member which is also provided. The second end of the elongated member would either be adapted for sealed engagement with the building water supply spigot, or with a provided reservoir and pump.

Further, the device may also be employed to provide a purified water supply to users by engagement of a spigot with the first end of the elongated member. The second end of the elongated member in this case would be in sealed engagement with the flexible tube which would be in sealed engagement with a purified water supply from a filter or reverse osmosis unit. This would allow the user to locate a purified water supply under the counter top which may be communicated above the counter top without the need to drill holes or apertures in the counter top. Further, if the elongated member has an axial passage that is divided into two passages and two engagement points are provided at the first end, which communicate respectively with a pressurized fluid supply and a purified water supply below the counter top, the use would.

Be provided with both without the need to cut holes in the counter. The elongated member would still translate to operate the drain and during installation would replace the drain rod of the existing faucet.

Still further, it is envisioned that the device can be provided in combination with a complete faucet assembly for both new and retrofit of an existing sink. In this manner the faucet will incorporate the elongated member with axial fluid passage adapted at an upper end for engagement to a water using device such as a dispenser or the aforementioned oral hygiene unit. The second end of the elongated member would either be adapted for sealed engagement with the building water supply spigot or with a reservoir and pump. In this mode of the device, the faucet would be manufactured and supplied with the elongated member and the other components sold separately or they could be provided with the new faucet as a unit and also with the dental hygiene or other device.

Accordingly, it is an object of the invention to provide an apparatus and system that allows a pressurized fluid supply from below a countertop-mounted sink, to be communicated above the counter top without cutting a hole in the counter top.

Another object of this invention is to provide such an apparatus and system, which is adapted to replace existing drain rods of existing faucets and also operate the drain for the sink.

An additional object of this invention is to provide such an apparatus and system as a complete faucet in combination with or adapted to engage oral hygiene devices with a fluid supply running through the drain rod control of the faucet.

A further object of this invention is to provide an apparatus and system which allows for removable engagement of the device above the sink and counter top, with a first end of the elongated member installed to replace the faucet drain activation rod.

Still another object of this invention is to provide an apparatus and system for a pressurized fluid supply above a sink counter which allows for multiple devices requiring pressurized fluid to removably engage with an elongated member adapted to replace the faucet drain rod.

These together with other objects and advantages which become subsequently apparent reside in the details of the construction and operation as more fully hereinafter described and claimed, reference being had to the accompanying drawings forming a part thereof, wherein like numerals refer to like parts throughout.

BRIEF DESCRIPTION OF THE DRAWING FIGURES

In the drawing figures, which are not to scale, and which are merely illustrative and wherein like reference characters denote similar elements throughout the several views:

FIG. 1 is a view of the device with all components featuring a pressurized fluid appliance in the form of a hand-held water jet oral hygiene device, engaged to a pressurized fluid supply through an elongated member in translateable engagement with a faucet and adapted to operate a drain.

DETAILED DESCRIPTION OF THE PREFERRED EMBODIMENTS

Referring now to the drawings the FIGURE discloses the preferred embodiments of the disclosed device 10 for providing a pressurized fluid supply for oral hygiene or other uses, above a counter top 12, by communication of the fluid supply through an elongated member 14 adapted for translatable engagement through the drain rod passage 16 of a conventional faucet 18 with a water supply conduit 19.

The elongated member 14 is provided for all embodiments of the device 10 for retrofitting either existing appliances 15, requiring a pressurized fluid supply, or when supplied as a complete unit with the oral hygiene or other device. It communicates the pressurized fluid supply from below a sink 11 or counter top 12 to the surface above, without the need to cut a hole or pathway through the counter top 12 or engaged sink.

The elongated member 14 in all embodiments has a fluid passage 20 communicating axially therethrough from a first end 22 to a second end 24. The elongated member has a circumference adapted to translatably engage through the drain rod passage 16 in a conventional faucet 18 that provides for drain activation of a sink mounted drain. In a particularly preferred mode of the device, it is employed in combination with, and to operate with a new or existing pulsating dental hygiene appliance 15 or other dental hygiene appliances requiring a pressurized water supply. It can be provided with the appliance 15 in a new installation, or where the user might want to relocate a reservoir or avoid cutting holes in the counter top 12, the elongated member 14 is provided as a retrofit adapted to engage with existing pulsating dental hygiene devices 15. As noted, it can also be provided with a complete faucet for new or retrofit construction.

In this embodiment, the first end 22 would be adapted for sealed communication with the intended oral hygiene or other device to be employed above the counter top 12. Most such appliances 15 such as a Waterpik or a purified water dispenser, have a flexible hose 38 that engages with a counter top supported reservoir. (Not shown). As a retrofit to existing pulsating dental hygiene devices 15 the device 10 would be provided with the elongated member 14 adapted at the first end 22 for a sealed engagement with the intended existing appliance hose 38. Adaptors can be included to adapt a plurality of different pulsating hygiene appliances 15 to engage with the elongated member 14.

The second end 24 would be adapted for sealed engagement to a flexible conduit 26 using means for sealed engagement to the flexible conduit 26 such as fitting 25 engaged with threads or compression engaged fittings 25 and "O" rings and the like. The conduit 26 would employ a mating fitting 29 to engage the fitting 25 on the member 14. The opposite end of the flexible conduit 26 would engage either a fitting 28 adapted to interface with a water spigot 30, or with the existing reservoir of the appliance so that it may be relocated below the counter top 12 without drilling holes in it. When engaged to a spigot 30, in the preferred mode of the device 10, the conduit 26 will engage both the hot water and cold water spigots 30 to allow for the water communicated to the elongated member 14 to be warm if desired. If both hot and cold water are communicated to the member 14, means to proportion the amount of hot to cold water will also be provided to allow the user to adjust the fluid temperature communicated to the member 14 and to the mouth. This can be done with a user operable gate valves which the user would adjust to proportion the hot and cold water. A combiner fitting 27 could be employed for this purpose where the hot and cold water would be communicated from the respective spigots 30 and combined in an internal conduit of the fitting 27 and communicated to the member 14. Valves 31 or other proportioning means for hot and cold proportioning to adjust dispersed fluid temperature can be included in the fitting 27 and adjusted by the user.

Also provided in all embodiments is a means for the elongated member 14 to operatively connect with the existing drain activation lever 32 so that translating the elongated member 32 operates to open and close the drain 34. This would allow the user to remove an existing drain activation rod and replace it with the elongated member 14 and to which the appliance 15 would be engaged to the first end 22 and the pressurized fluid supply to the second end 24. The engagement at the first end 22 may be permanent, or in a particularly preferred mode, the first end 22 would be removably engaged to allow the user to either engage multiple water using devices to the first end 22 or to at least disconnect the one employed.

Embodiments of the device 10 with the removable means of sealed engagement at the first end 22 with a conduit supplying a pressurized water using appliance, would in a preferred mode, feature an engagement aperture 34 located at the first end 22 communicating with the axial fluid passage 20. The engagement aperture 34 is adapted for a sealed, removable engagement with a plug 36 or nipple 37 on the distal end of the hose 38 communicating with the appliance requiring water or fluid. The plug 36 engaged into the engagement aperture 34 thereby provides a removable sealed communication of fluid from the axial passage 20 to the hose 38 or other conduit supplying the appliance 15. Once the plug 36 is removed from the engagement aperture 34 it self-seals using means for self-sealing as would the plug 36 to avoid water flowing onto the countertop once removed. This can be accomplished by means to prevent backflow such as a one way flow valve 35 operatively positioned in the hose 38 or the plug 36. Additionally, while the specification defines the components as a plug 36 and aperture 34, those skilled in the art will realize that components of other dimension and configuration can be employed so long as they provide a means of sealed engagement of the hose 38 to the fluid passage 20 and all such means as would occur to those skilled in the art are anticipated within the scope of this invention.

The second end 24 of the elongated member 14 connects to the flexible conduit 26 or conduit using means of sealed engagement therewith. This sealed engagement may be threaded or may be similar to the removable engagement at the first end or an engagement that those skilled in the art might employ. As noted, the sealed engagement may be adapted to communicate with the reservoir of an existing appliance 15 or provided as a complete appliance in a kit of components.

In a particularly preferred mode of the device 10 all the appropriate components for the user would be provided including the appliance 15, the hose 38 supplying it, the elongated member 14 adapted to translate in the faucet 18 and flexible conduit 26 adapted with means for sealed engagement between the second end of the member 14 and a fluid supply. The conduit 26 would be flexible to allow translation of the elongated member 14 to operate the drain 24. The opposite end of the conduit 26 would engage either a pump-energized reservoir, a water filtering unit, or the existing water spigot 30 under the counter top 12.

If a continuous pressurized water supply is required for the water filtering device, the reservoir, or for direct communication to the supplied appliance 15, a means to engage the water supply from the spigot 30 would also be provided. A current preferred such means to engage the water supply is the fitting 28 adapted for sealed engagement between flexible conduit 26 and the threaded outlet aperture of the spigot 30.

As noted the elongated member 14 is adapted to translate in the faucet and replaces the existing drain rod in a retrofit, or can also be provided with new faucets 18 as a unit to provide a path for a pressurized fluid supply for an original installation. Since it must operate the drain 34, a central portion of the elongated member 14 is adapted adjacent to the second end 24 using means for operative engagement with a drain plug activation rod 32 of a conventional sink drain. Such a means for engagement with the activation rod can be an angled member 40 which is engaged at one end to the elongated member 14 and at the other to the activation rod 32. Other means for engagement which would occur to those skilled in the art are anticipated.

The device, when provided with all components as a complete appliance for oral hygiene would also provide the appliance 15. In a particularly preferred mode of the device 10, the appliance 15 supplied would have a water jet 42 at the end of a handle component which would receive pressurized fluid through the hose 38 from the first end of the elongated member 14.

Further, the device 10 may also be provided as a complete kit of components employed to provide a purified water supply to users by engagement of a water dispenser 44 with the first end 22 of the elongated member 14. The flex conduit 26 would be engaged to a supplied means for filtration of water such as a filter 45 or reverse osmosis component. The filter 45 or other means of filtration can of course be employed with any mode of the device with or without the water dispenser 44 to provide a cleaner tasting and more sanitary stream of water from the water jet 42 when employed for gum massage and teeth cleaning. The filter 45 may be mounted anywhere so long as it is inline to filter the water communicated to the flex conduit 26 and can thus be attached to the fitting 27 or plumbed into it or in-between the water from the spigots 30 and the flexible conduit 26. If provided in a kit, the device 10 would include one or a combination of the appliance 15, a water dispenser 44 operated by handle 51 or other mean of activation, and also a preferably decorative and easy to grip end plug 49 which can be engaged with the first end 22 of the elongated member 14 when either of the other supplied components are not.

Finally, as noted above, if the elongated member 14 is provided with two axial passages 20 and two respective engagement points at the first end 22, both a pressurized fluid supply and a purified water supply may be communicated to the second end 22 from below the counter top 12. Both would be provided without the need to drill into the counter top 12 for passageways.

Although the invention has been described with respect to particular embodiments thereof, it should be realized that various changes and modifications may be made therein without departing from the spirit and scope of the invention. While the invention as shown in the drawings and described in detail herein discloses arrangements of elements of particular construction and configuration for illustrating preferred embodiments of structure and method of operation of the present invention, it is to be understood, however, that elements of different construction and configuration and other arrangements thereof, other than those illustrated and described, may be employed in accordance with the spirit of this invention. Any and all such changes, alternations and modifications as would occur to those skilled in the art are considered to be within the scope of this invention as broadly defined in the appended claims.

Further, the purpose of the attached abstract is to enable the U.S. Patent and Trademark Office and the public generally, and especially the scientists, engineers and practitioners in the art who are not familiar with patent or legal terms or phraseology to determine quickly from a cursory inspection the nature and essence of the technical disclosure of the application. The abstract is neither intended to define the invention of the application, which is measured by the claims, nor is it intended to be limiting as to the scope of the invention in any way.

What is claimed is:

1. An apparatus for communication of a pressurized water supply above a counter top having a sink engaged therein and having a faucet with a water supply conduit for providing water to the sink, said faucet engaging to one of said sink or said counter top and having a drain rod passage, said sink further includes a drain allowing collected water to drain out and a drain lever for opening and closing said drain, the apparatus comprising:

an elongated rod having a first end, a second end, and a central portion defining an axial water passageway which allows water to flow from said second end to said first end; said central portion is formed between said first end and said second end; said elongated rod is designed for translatable engagement in said drain rod passage of said faucet in an engaged position; said drain rod passage is communicating from above said counter top to a cavity below said counter top and said sink; said elongated rod having an exterior circumference designed to fit through said drain rod passage of said faucet and said cavity such that said first end of said elongated rod extends above said faucet, said sink and said counter top and said second end of said elongated rod extends through said cavity below said faucet, said sink and said counter top; wherein said drain lever is designed to engage said central portion of said elongated rod when in said engaged position so that the translation of said elongated rod causes the activation of said drain lever to close and open said drain;

a water spraying appliance is removably attached to said first end of said elongated rod; and a pressurized water supply is connected to said second end of said rod; said pressurized water supply located below said counter top when said elongated rod is in said engaged position, whereby said pressurized water supply is supplying water through said axial water passageway of said elongated rod to said water spraying appliance which is engaged to said first end of said elongated rod in said engaged position.

2. The apparatus of claim 1 wherein said water spraying appliance comprises:

a dental sprayer, said dental sprayer directing said fluid supply in a pulsating fluid stream from a spraying head engaged to a fluid passage communicating through a sprayer body; and said input conduit being a hose engaged to said fluid passage on a first end and having a second end adapted for engagement to said first end of said rod.

3. The apparatus of claim 2, wherein said hose is removed from said engagement to said first end of said rod.

4. The apparatus of claim 3 wherein said pressurized water supply located below said counter top comprises:

a flexible conduit having an axial passage therethrough communicating from said first end to a second end;

means for sealed engagement of said second end of said rod, to said first end of said flexible conduit; and means for sealed engagement of said second end of said flexible conduit, to said pressurized fluid supply in said cavity.

5. The apparatus of claim 4 wherein said means for sealed engagement of said second end of said flexible conduit, to said pressurized water supply in said cavity comprises:

a fitting adapted to engage upon a water spigot located in said cabinet;

said fitting adapted to bifurcate pressurized water from said spigot into two fluid streams, a first of said fluid streams communicating with said faucet, a second of said fluid streams communicating with said second end of said flexible conduit.

6. The apparatus of claim 5 wherein said means for sealed engagement of said second end of said flexible conduit, to said pressurized water supply in said cavity additionally comprises:

a second fitting adapted to engage upon a second spigot located in said cabinet;

said second fitting adapted to bifurcate a second supply of said pressurized water from said second spigot into two secondary fluid streams, a first of said secondary fluid streams communicating with said faucet, a second of said secondary fluid streams communicating with said second end of said flexible conduit;

said second fluid stream and said secondary fluid stream communicating with said second end of said flexible conduit thereby providing said pressurized fluid stream as a mixed fluid stream of hot water and cold water; and means to proportion the ratio of said second fluid stream and said secondary fluid stream communicated to form said mixed fluid stream thereby providing means to adjust a temperature of said pressurized fluid stream.

7. The apparatus of claim 3 wherein said water spraying appliance is one of a plurality of removably engageable appliances from a group consisting of a dental sprayer, a water dispenser, and a handle adapted for easy gripping by the hand.

8. The apparatus of claim 1 wherein said pressurized water supply located below said counter top comprises:

a flexible conduit having an axial passage therethrough communicating from said first end to a second end;

means for sealed engagement of said second end of said rod, to said first end of said flexible conduit; and means for sealed engagement of said second end of said flexible conduit, to said pressurized fluid supply in said cavity.

* * * * *